(12) United States Patent
Takami et al.

(10) Patent No.: US 9,795,437 B2
(45) Date of Patent: Oct. 24, 2017

(54) ELECTROSURGICAL TREATMENT SYSTEM

(71) Applicant: OLYMPUS CORPORATION, Hachioji-shi, Tokyo (JP)

(72) Inventors: Sadayoshi Takami, Hachioji (JP); Tsuyoshi Hayashida, Hachioji (JP)

(73) Assignee: OLYMPUS CORPORATION, Toyko (JP)

( * ) Notice: Subject to any disclaimer, the term of this patent is extended or adjusted under 35 U.S.C. 154(b) by 0 days.

(21) Appl. No.: 15/256,072

(22) Filed: Sep. 2, 2016

(65) Prior Publication Data
US 2016/0367308 A1    Dec. 22, 2016

Related U.S. Application Data

(63) Continuation of application No. PCT/JP2015/068782, filed on Jun. 30, 2015.

(30) Foreign Application Priority Data

Aug. 26, 2014 (JP) ................................ 2014-171968

(51) Int. Cl.
*A61B 18/10* (2006.01)
*A61B 18/12* (2006.01)
*A61B 18/00* (2006.01)

(52) U.S. Cl.
CPC .......... *A61B 18/1206* (2013.01); *A61B 18/12* (2013.01); *A61B 2018/00589* (2013.01);
(Continued)

(58) Field of Classification Search
CPC ................ A61B 18/12; A61B 18/1206; A61B 2018/00589; A61B 2018/00648;
(Continued)

(56) References Cited

U.S. PATENT DOCUMENTS

2004/0199179 A1* 10/2004 Elliott ................ A61B 18/1477
606/128
2006/0052661 A1* 3/2006 Gannot .................. A61B 1/042
600/108
(Continued)

FOREIGN PATENT DOCUMENTS

CN         102596078 A       7/2012
EP         2 319 447 A1      5/2011
(Continued)

OTHER PUBLICATIONS

Jun. 14, 2016 Office Action issued in Japanese Patent Application No. 2016-521377.
(Continued)

*Primary Examiner* — Daniel Fowler
(74) *Attorney, Agent, or Firm* — Oliff PLC

(57) ABSTRACT

An electrosurgical treatment system includes an output section that supplies a high-frequency output to a treatment instrument, a detecting section that detects a voltage and an electric current of the high-frequency output in the output section, a phase-difference detecting section that calculates a phase difference between the detected voltage and electric current, and a control section that switches, on the basis of a change in the phase difference, a first phase for drying a biological tissue by applying the high-frequency output to the biological tissue while increasing the voltage to a second phase for coapting the biological tissue by performing, with a set value of a voltage determined according to a voltage value of the high-frequency output at an end point in time of the first phase, constant voltage control.

13 Claims, 12 Drawing Sheets

(52) U.S. Cl.
CPC .............. *A61B 2018/00648* (2013.01); *A61B 2018/00767* (2013.01); *A61B 2018/00827* (2013.01); *A61B 2018/00869* (2013.01); *A61B 2018/00892* (2013.01)

(58) Field of Classification Search
CPC A61B 2018/00767; A61B 2018/00827; A61B 2018/00869; A61B 2018/00892
See application file for complete search history.

(56) References Cited

U.S. PATENT DOCUMENTS

| | | | |
|---|---|---|---|
| 2007/0123847 A1 | 5/2007 | Mihori | |
| 2007/0173803 A1* | 7/2007 | Wham | A61B 5/03 606/34 |
| 2007/0173811 A1* | 7/2007 | Couture | A61B 18/1445 606/39 |
| 2007/0276363 A1* | 11/2007 | Patton | A61B 18/1442 606/51 |
| 2008/0082098 A1* | 4/2008 | Tanaka | A61B 18/1206 606/41 |
| 2008/0103495 A1* | 5/2008 | Mihori | A61B 18/1206 606/38 |
| 2009/0048595 A1* | 2/2009 | Mihori | A61B 18/1206 606/49 |
| 2009/0248002 A1* | 10/2009 | Takashino | A61B 18/085 606/28 |
| 2009/0248007 A1 | 10/2009 | Falkenstein et al. | |
| 2009/0248013 A1 | 10/2009 | Falkenstein et al. | |
| 2009/0248019 A1 | 10/2009 | Falkenstein et al. | |
| 2009/0248020 A1 | 10/2009 | Falkenstein et al. | |
| 2009/0248022 A1 | 10/2009 | Falkenstein et al. | |
| 2010/0042101 A1* | 2/2010 | Inagaki | A61B 18/1442 606/52 |
| 2010/0185196 A1* | 7/2010 | Sakao | A61B 18/1445 606/51 |
| 2012/0136345 A1 | 5/2012 | Takashino | |
| 2012/0136347 A1 | 5/2012 | Brustad et al. | |
| 2014/0066927 A1 | 3/2014 | Brustad et al. | |

FOREIGN PATENT DOCUMENTS

| | | |
|---|---|---|
| EP | 2 335 631 A2 | 6/2011 |
| EP | 2 359 762 A2 | 8/2011 |
| EP | 2 364 662 A1 | 9/2011 |
| EP | 2 465 458 A1 | 6/2012 |
| EP | 2 664 287 A1 | 11/2013 |
| EP | 2 856 961 A1 | 4/2015 |
| JP | 2003-284725 A | 10/2003 |
| JP | 2007-143878 A | 6/2007 |
| JP | 2009-045456 A | 3/2009 |
| JP | 4 567 811 B2 | 10/2010 |
| JP | 2011-526157 A | 10/2011 |
| JP | 2013-542765 A | 11/2013 |
| JP | 2015-110063 A | 6/2015 |
| WO | 2009/124097 A1 | 10/2009 |
| WO | 2011/018844 A1 | 2/2011 |
| WO | 2012/045095 A1 | 4/2012 |

OTHER PUBLICATIONS

Oct. 6, 2015 International Search Report issued in Patent Application No. PCT/JP2015/068782.

* cited by examiner

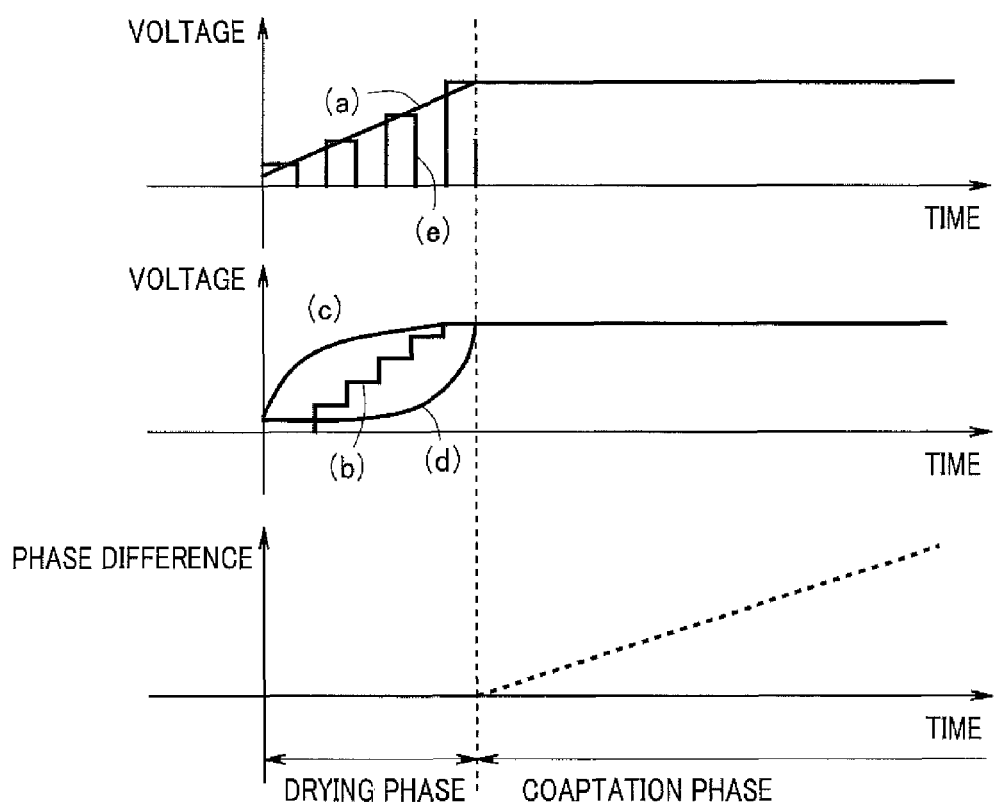
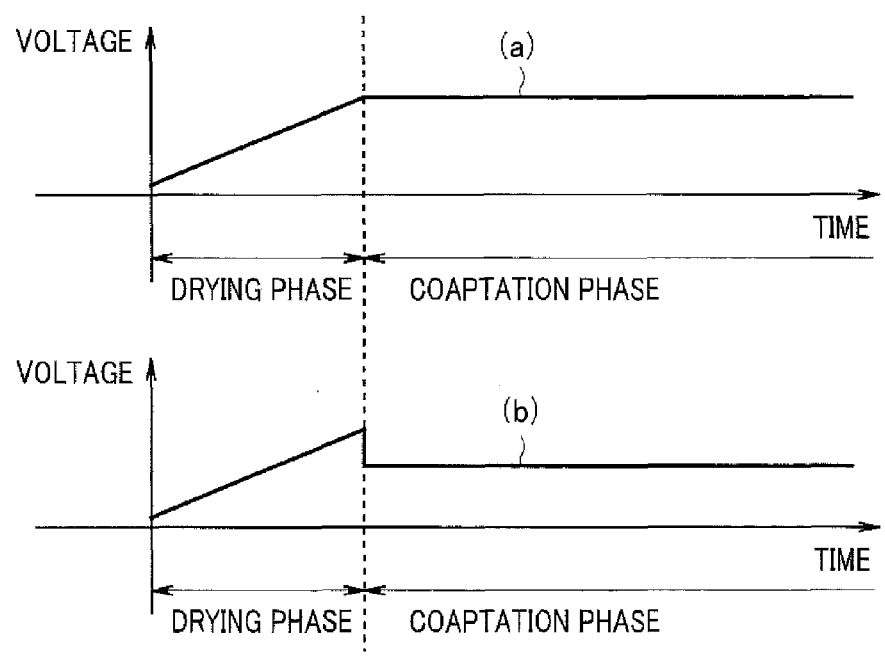

ELECTROSURGICAL TREATMENT SYSTEM

CROSS REFERENCE TO RELATED APPLICATION

This application is a continuation application of PCT/JP2015/068782 filed on Jun. 30, 2015 and claims benefit of Japanese Application No. 2014-171968 filed in Japan on Aug. 26, 2014, the entire contents of which are incorporated herein by this reference.

BACKGROUND OF THE INVENTION

1. Field of the Invention

The present invention relates to an electrosurgical treatment system for coapting a biological tissue.

2. Description of the Related Art

An electrosurgical treatment system such as an electric knife has been used when treatment such as dissection, coagulation, or hemostasis of a biological tissue is performed in a surgical operation or the like. Such an electrosurgical treatment system includes, for example, a high-frequency power supply that outputs high-frequency power and a treatment instrument connected to the high-frequency power supply.

When coagulation or hemostasis of a biological tissue is performed using the electrosurgical treatment system, it is known that a dehydrated state of a target region and a bonded state of the target region are closely related. That is, as the dehydrated state of a biological tissue of the target region is closer to perfection, certainty of the bonded state of the target region is further improved.

In a high-frequency treatment apparatus, a biological tissue is treated by, for example, grasping the biological tissue with a pair of electrodes and applying a high-frequency wave to the grasped biological tissue. In such a high-frequency treatment apparatus, impedance of the grasped biological tissue is measured and a current value, a voltage value, a power value, a frequency, and the like of the high-frequency wave applied to the biological tissue are controlled on the basis of the measured impedance to perform appropriate treatment.

Japanese Patent No. 4567811 discloses an electric surgical apparatus that calculates impedance of a biological tissue and, when the impedance exceeds a predetermined threshold, performs control for increasing a high-frequency power frequency stepwise to enable sure treatment.

Japanese Patent Application Laid-Open Publication No. 2009-45456 discloses a technique for determining, according to a phase difference between a voltage and an electric current of an output, switching from a cauterization process for coaptation to a dehydration process of a coapted part.

SUMMARY OF THE INVENTION

An electrosurgical treatment system according to an aspect of the present invention includes: a high-frequency-power generating section that generates a high-frequency output for treating a biological tissue; an output section that supplies the high-frequency output to the treatment instrument that applies the high-frequency output to the biological tissue; a detecting section that detects a voltage and an electric current of the high-frequency output in the output section; a phase-difference detecting section that calculates a phase difference between the voltage and the electric current detected by the detecting section; and a control section that controls the high-frequency-power generating section and switches, on the basis of a change in the phase difference, a first phase for drying the biological tissue by applying the high-frequency output in the output section to the biological tissue while increasing the voltage with respect to a start time to a second phase for coapting the biological tissue by performing, with a set value of a voltage determined according to a voltage value at an end point in time of the first phase, constant voltage control of the high-frequency output applied to the biological tissue.

BRIEF DESCRIPTION OF THE DRAWINGS

FIG. 6 is an explanatory diagram for explaining control for a first phase;

FIG. 7 is an explanatory diagram for explaining control for a second phase;

DETAILED DESCRIPTION OF THE PREFERRED EMBODIMENT(S)

Embodiments of the present invention are explained in detail below with reference to the drawings.

First Embodiment

Figure 1:
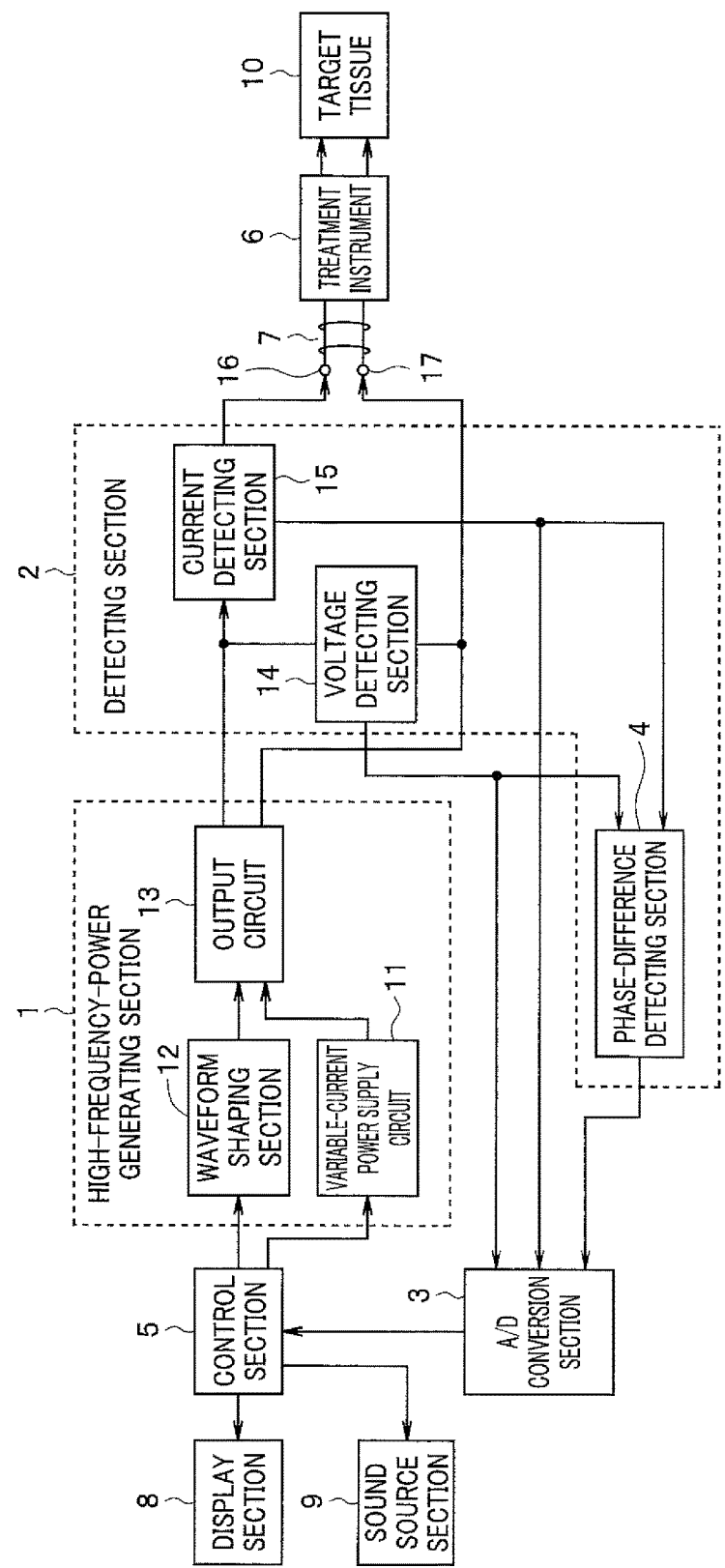
FIG. 1 is a block diagram showing an electrosurgical treatment system according to a first embodiment of the present invention.

FIG. 1 is a block diagram showing an electrosurgical treatment system according to a first embodiment of the present invention. The electrosurgical treatment system according to the present embodiment includes, for example, a treatment instrument (forceps, etc.) of a bipolar type and a high-frequency power supply that is electrically connected to the treatment instrument and outputs energy for causing the treatment instrument to operate. The electrosurgical treatment system feeds a high-frequency current from the high-frequency power supply to the treatment instrument to thereby perform dissection, coagulation (drying and coaptation), and the like of a biological tissue set as a treatment target (hereinafter referred to as target tissue) 10. In the electrosurgical treatment system in the present embodiment, it is possible to perform treatment by two phases in which output control for a high-frequency output is different. Switching timing of the respective phases is controlled on the basis of a phase difference between a voltage and an electric current of the high-frequency output. Subsequent output control of the phases is performed according to, for example, a level of the high-frequency output at the phase switching timing. Note that, as a control method for energy of the high-frequency output to a biological tissue, voltage control is mainly explained as an example in the specification. However, power control is also possible.

In FIG. 1, the electrosurgical treatment system (the high-frequency power supply) includes at least a high-frequency-power generating section 1 that generates a high-frequency output, a detecting section 2 that detects an electric current, a voltage, and a phase difference from the outputted high-frequency output, and a control section 5 that performs control of the entire system.

A waveform shaping section 12 of the high-frequency-power generating section 1 is controlled by the control section 5 explained below to generate a driving waveform. A set value is given to a variable DC power supply circuit 11 of the high-frequency-power generating section 1 from the control section 5. The variable DC power supply circuit 11 supplies a DC voltage of a level based on the set value to an output circuit 13. The output circuit 13 generates a high-frequency output, a level of a driving waveform of which is specified by an output of the variable DC power supply circuit 11, and outputs the high-frequency output from an output end.

One output end of the output circuit 13 is connected to an output terminal 16 via a current detecting section 15. The other output end is directly connected to an output terminal 17. A treatment instrument 6 is connected between the output terminals 16 and 17 via a cable 7. The treatment instrument 6 is enabled to apply the high-frequency output from the output circuit 13 propagated by the cable 7 to the target tissue 10 and perform treatment. A voltage detecting section 14 is connected between both output ends of the output circuit 13.

The voltage detecting section 14 detects an output voltage of the output circuit 13. The current detecting section 15 detects an output current of the output circuit 13. Respective detection results of the voltage detecting section 14 and the current detecting section 15 are supplied to an A/D conversion section 3 and a phase-difference detecting section 4. The phase-difference detecting section 4 detects a phase difference between a voltage and an electric current of the high-frequency output outputted from the output circuit 13 and outputs the phase difference to the A/D conversion section 3. The A/D conversion section 3 converts inputted respective signals into digital signals and outputs the digital signals to the control section 5. Note that the detecting section 2 is configured by the voltage detecting section 14, the current detecting section 15, and the phase-difference detecting section 4.

The control section 5 can be configured by a not-shown processor and the like. The control section 5 performs control of the entire system. The control section 5 is configured to control outputs of the waveform shaping section 12 and the variable DC power supply circuit 11 of the high-frequency-power generating section 1 and control a waveform and a level of the high-frequency output. The control section 5 is configured to feedback-control the waveform shaping section 12 and the variable DC power supply circuit 11 such that a voltage signal and a current signal are fed back from the A/D conversion section 3 and a set high-frequency output is obtained.

The control section 5 controls the high-frequency-power generating section 1 to enable treatment by two phases, in which controls are different, for the target tissue 10. The control section 5 adopts, for example, as a first phase, a drying phase for drying the target tissue 10. The control section 5 adopts, for example, as a second phase, a coaptation phase for coapting the target tissue 10.

In the present embodiment, the control section 5 is configured to control switching timing from the first phase to the second phase on the basis of a phase difference signal from the A/D conversion section 3.

The treatment instrument 6 includes a pair of grasping members respectively connected to the output terminals 16 and 17. The treatment instrument 6 grasps the target tissue 10 with the pair of grasping members to apply a high-frequency output to the target tissue 10. High-frequency outputs from the output terminals 16 and 17 are transmitted to the respective grasping members of the treatment instrument 6 via the cable 7. When an actual situation of use is taken into account, the cable 7 has length of, for example, approximately 3 m. An inductance component corresponding to the cable 7 is present in the cable 7.

A capacitance component by the target tissue 10 is generated between the pair of grasping members that is grasping the biological tissue 10. Whereas the inductance component of the cable 7 is substantially fixed, the capacitance component between the grasping members changes according to a state of the target tissue 10. That is, in a state in which the target tissue 10 has a relatively high moisture content, a value of the capacitance component is small. The capacitance component increases when air bubbles or the like occur as drying of the target tissue 10 advances. Then, as the drying of the target tissue 10 advances, influence of the capacitance component between the grasping members increases with respect to the inductance component of the cable 7. In the high-frequency output, a phase of an electric current gradually advances on the basis of a voltage.

For example, in the state in which the target tissue 10 has a relatively high moisture content, the phase of the electric current of the high-frequency output is delayed compared with a phase of the voltage. When the drying of the target tissue 10 advances, the phase of the electric current with respect to the voltage also advances accordingly, the phases of the voltage and the electric current coincide with each other, and, further, the phase of the electric current further advances than the phase of the voltage.

Impedance of a biological tissue is relatively greatly affected by a dried state of a biological tissue surface. Therefore, the dried state of the biological tissue cannot be accurately grasped with only the impedance. On the other hand, the phase difference between the voltage and the electric current of the high-frequency output is a value reflecting the dried state of the entire target tissue 10. A degree of a change in the phase difference is different depending on a volume, quality, and the like of the target tissue 10. However, a relation between the value of the phase difference and the dried state substantially corresponds to a one-to-one relation irrespective of a volume and quality of the biological tissue. Therefore, it is possible to determine that the target tissue 10 has reached a predetermined dried state at timing when the phase difference between the voltage and the electric current of the high-frequency output has reached a predetermined value or timing when the phase difference between the voltage and the electric current of the high-frequency output indicates a predetermined change. This determination is considered to be more accurate than determination performed using only the impedance.

The control section 5 may set, as a transition condition for phase switching, the phase difference between the voltage and the electric current of the high-frequency output reaching the predetermined value after treatment in the first phase is started, determine that the target tissue 10 has reached the predetermined dried state when the transition condition is satisfied, and switch the first phase to the second phase. Note that the control section 5 reads out the transition condition stored in a not-shown memory to determine switching timing. The user can store the transition condition in the memory as appropriate with a not-shown input device.

In the present embodiment, the control section 5 may set, as the transition condition, for example, the phase difference between the voltage and the electric current of the high-frequency output reaching 0 or a range near 0 or leaving 0 or the range near 0 and set, as the switching timing from the first phase to the second phase, a point in time when the transition condition is satisfied. Note that the control section 5 may change the transition condition according to a type of a treatment instrument, a type of a biological tissue, and the like. For example, the control section 5 may appropriately change, for each of types of treatment instruments, a value of a phase difference set for the switching timing from the first phase to the second phase. Not only this but, as explained below, it is possible to set various transition conditions based on the phase difference.

Figure 2A:
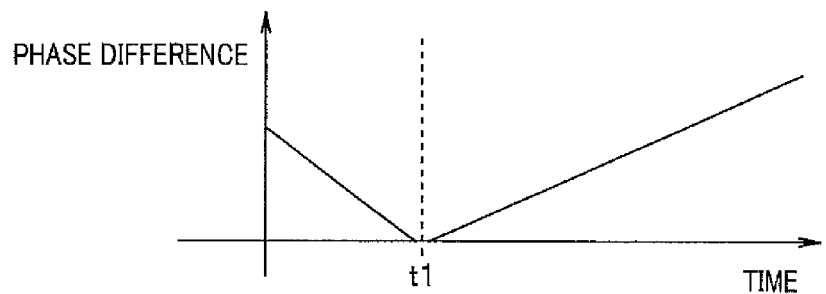
FIG. 2A is a graph showing a change in a phase difference with time plotted on a horizontal axis and the phase difference plotted on a vertical axis.
Figure 2B:
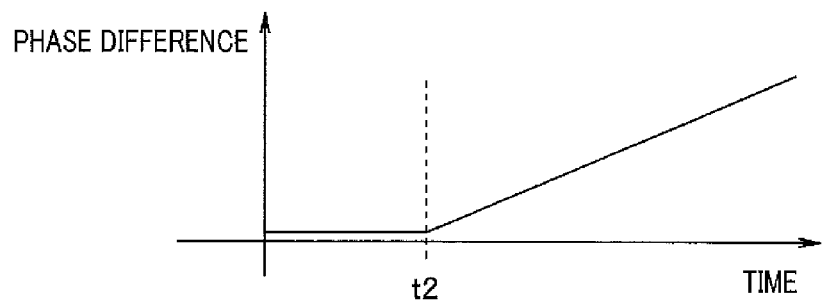
FIG. 2B is a graph showing a change in a phase difference with time plotted on a horizontal axis and the phase difference plotted on a vertical axis.

FIG. 2A and FIG. 2B are graphs showing changes in the phase difference with time plotted on horizontal axes and the phase difference plotted on vertical axes. FIG. 2A and FIG. 2B respectively show changes in the phase difference between the voltage and the electric current of the high-frequency output in cases in which the high-frequency output having a fixed voltage value is applied to tissues different from each other. Note that the vertical axes of FIG. 2A and FIG. 2B show an absolute value of the phase difference.

In an example shown in FIG. 2A, the absolute value of the phase difference is relatively large at a treatment start point in time. The absolute value of the phase difference decreases as time elapses and reaches a minimum value at time t1. After elapse of time t1, a phase of the electric current further advances and the phase difference increases. Note that FIG. 2B indicates that the change in the phase difference from the treatment start point in time to time t2 is small and the absolute value of the phase difference increases from a point in time of time t2. The control section 5 sets, for example, timings of times t1 and t2 in FIG. 2A and FIG. 2B as the switching timing from the first phase to the second phase.

That is, usually, from a start of the drying phase, the absolute value of the phase difference decreases or stabilizes at a relatively low value. As dehydration and drying of the tissue advance, the absolute value of the phase difference increases. By detecting such a change in the absolute value of the phase difference, switching from the first phase to the second phase is performed. At a point in time of the switching from the first phase (the drying phase) to the second phase (the coaptation phase), the target tissue 10 is in a sufficiently dried state. It is easy to control coaptation treatment in the coaptation phase.

Further, in the present embodiment, treatment in the second phase is controlled according to a control state until an end of the first phase, for example, a control state at an end point in time of the first phase. A time period required until the phase difference between the voltage and the electric current of the high-frequency output reaches the predetermined value (a period length of the first phase) is different according to differences in thickness and the like of the target tissue 10. In the first phase, a high-frequency output level (a voltage) is changed as time elapses. In this case, the voltage of the high-frequency output at the end point in time of the first phase is different in each of treatment target tissues according to the difference in the first phase period length. Note that, even when the high-frequency output is fixed, high-frequency output energy applied to the treatment target tissues in the first phase period is different in each of the tissues.

In the present embodiment, the control in the first phase period is control necessary for changing a treatment target biological tissue to a specified dried state. Therefore, control corresponding to the control in the first phase period is applied to the second phase period as well to enable sure treatment for a treatment target tissue irrespective of thickness and the like of the target tissue 10. For example, in the present embodiment, when the control section 5 performs control for applying a high-frequency output having a voltage value increasing according to elapse of time to the target tissue 10 in the first phase, in the second phase, the control section 5 may apply a high-frequency output maintaining a voltage value at the end point in time of the first phase to the target tissue 10.

Note that specific control and phase end control in the first phase and the second phase are explained below.

Figure 3:
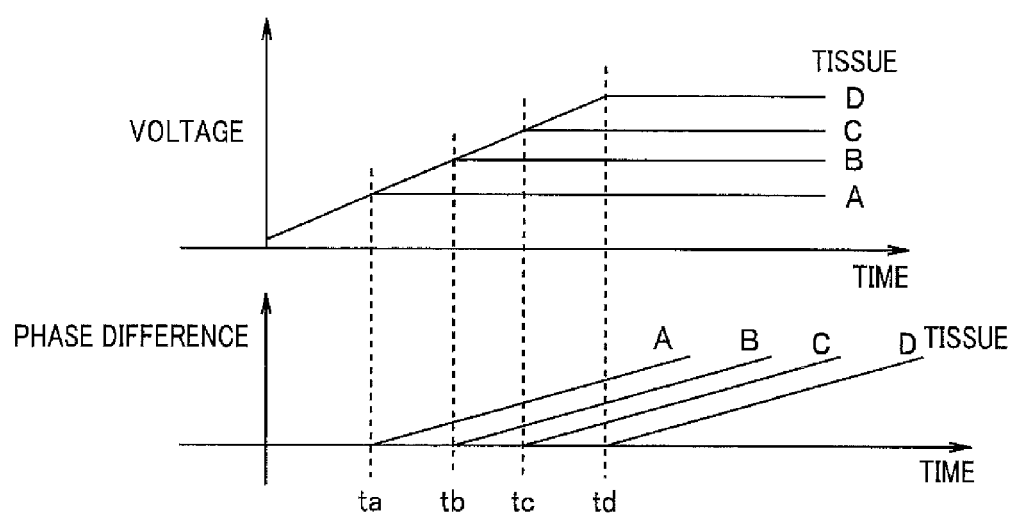
FIG. 3 is an explanatory diagram showing voltage control performed when biological tissues A to D are adopted as a target tissue 10.

FIG. 3 is an explanatory diagram showing voltage control performed when biological tissues A to D are adopted as the target tissue 10. An upper part of FIG. 3 shows a relation between elapse of time and a change in the voltage with time plotted on a horizontal axis and the voltage plotted on a vertical axis. A lower part of FIG. 3 shows a change in the phase difference with time plotted on a horizontal axis and the phase difference plotted on a vertical axis. In the lower part of FIG. 3, an increase in the phase difference from a minimum value is set as the transition condition. The lower part of FIG. 3 shows an example in which timing when the phase difference increases from the minimum value is set as the switching timing from the first phase to the second phase. Switching timings concerning the biological tissues A to D are respectively ta, tb, tc, and td.

As shown in the upper part of FIG. 3, at a start point in time of the first phase period, a high-frequency output having the same voltage value is applied to all of the biological tissues A to D. The control section 5 increases the voltage value of the high-frequency output applied to the biological tissues A to D until the switching timings ta to td come and the first phase period ends. An example is shown in which a rate of increase of the voltage value shown in FIG. 3 is the same in the respective biological tissues A to D.

At time ta, concerning the biological tissue A, the control section 5 determines that drying has ended and ends the first phase period. The control section 5 shifts to the second phase period in a state in which a voltage of the high-frequency voltage at the end point in time of the first phase is maintained. Consequently, as shown in the upper part of FIG. 3, a voltage value of the high-frequency output applied to the biological tissue A is fixed at time ta and subsequent times.

Similarly, at times tb to td, concerning the biological tissues B to D, the control section 5 determines that drying has ended and ends the respective first phase periods. The control section 5 shifts to the second phase period in a state in which a voltage of the high-frequency voltage at the end point in time of the first phase is maintained. Consequently, as shown in the upper part of FIG. 3, voltage values of the high-frequency output applied to the respective biological tissues B to D in the second phase are maintained at respective voltage values applied at the end point in time of the first phase.

A display section 8 is controlled by the control section 5 to be capable of displaying an inputted instruction, an apparatus state, and a treatment (process) situation. A sound source section 9 is controlled by the control section 5 to be capable of notifying an operator of the inputted instruction, the apparatus state, and the treatment (process) situation with buzzer sound (including chime sound) or voice.

Figure 4:
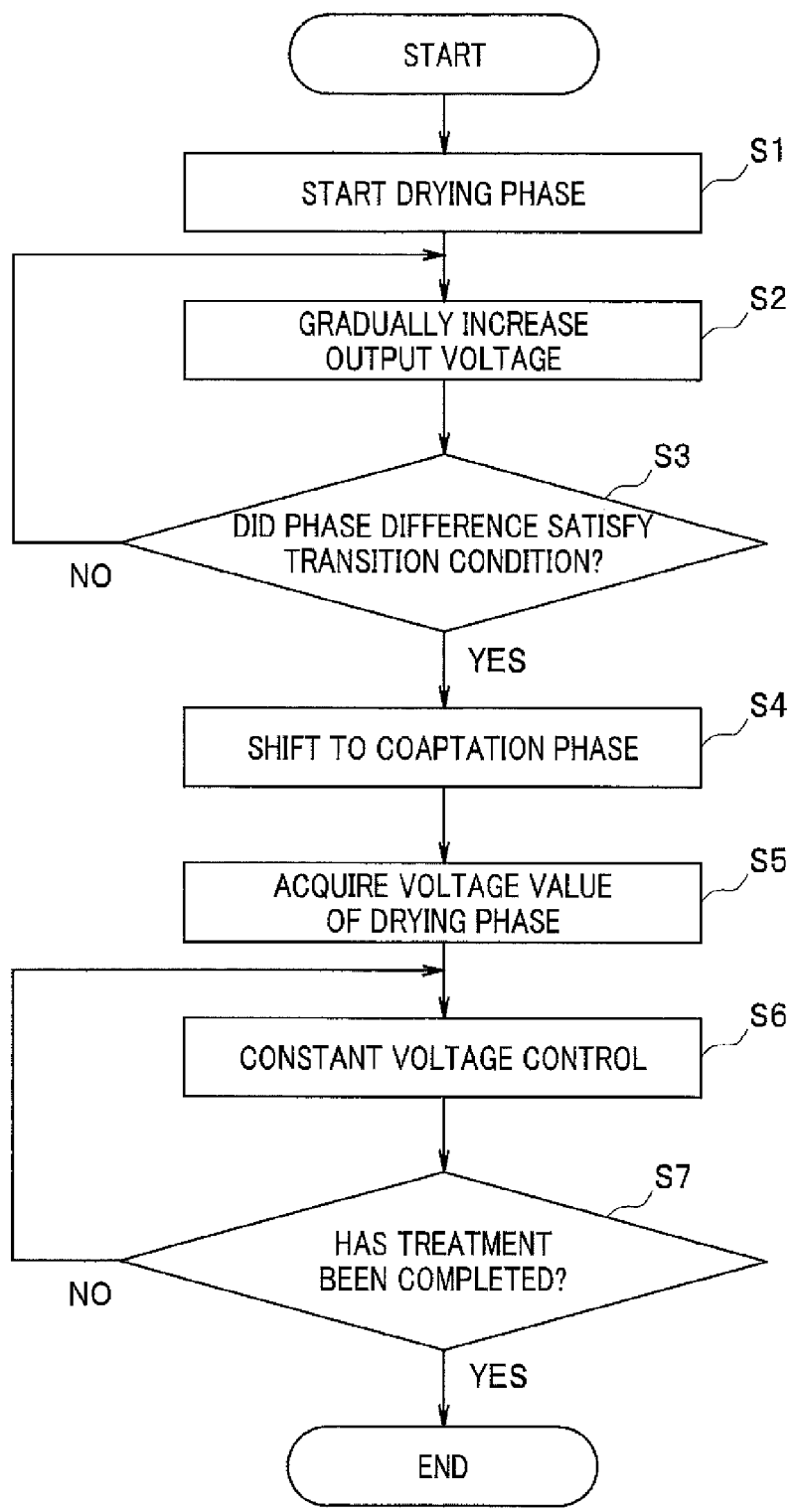
FIG. 4 is a flowchart for explaining an operation in the first embodiment.
Figure 5:
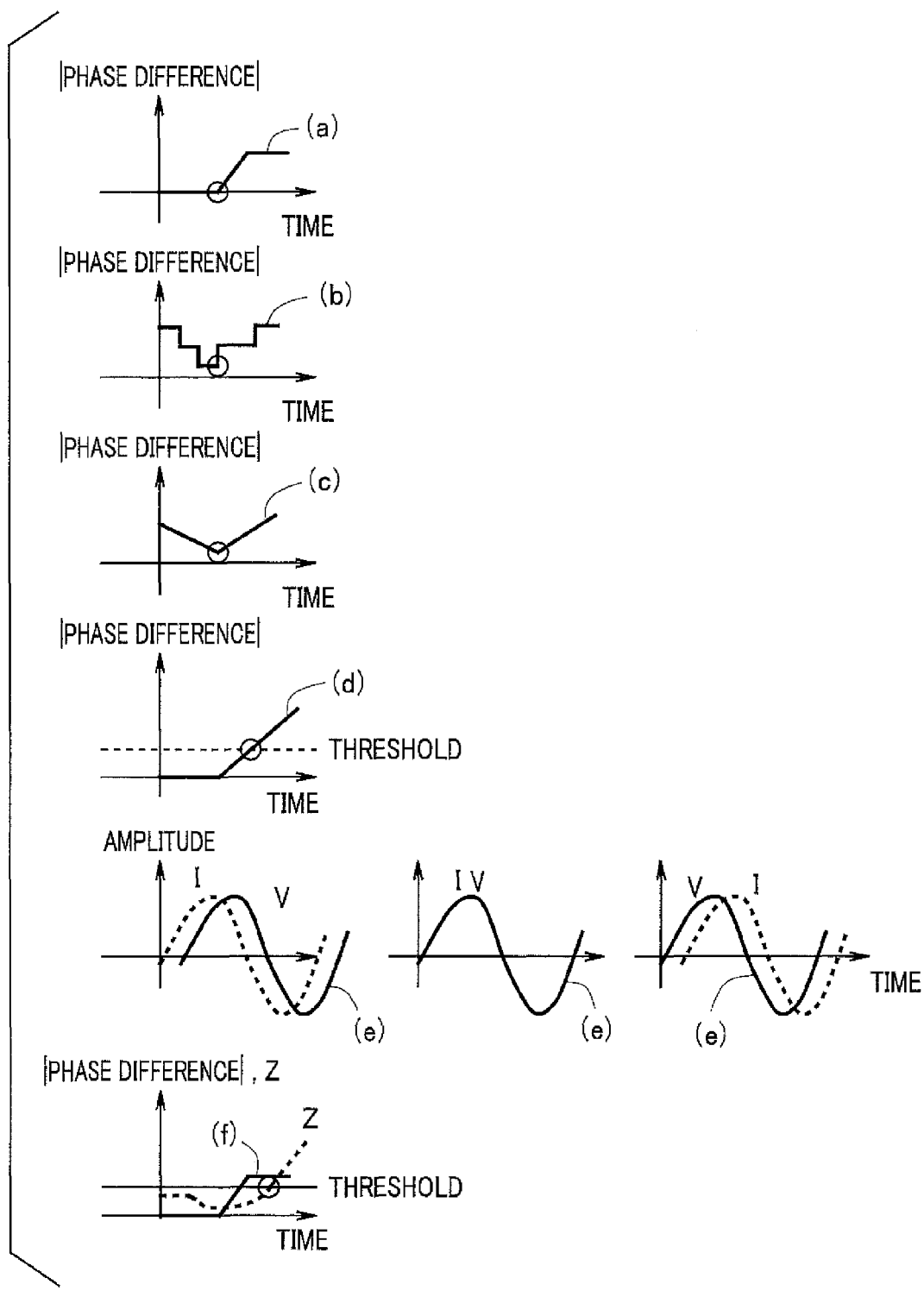
FIG. 5 is an explanatory diagram for explaining a phase switching method.
Figure 8:
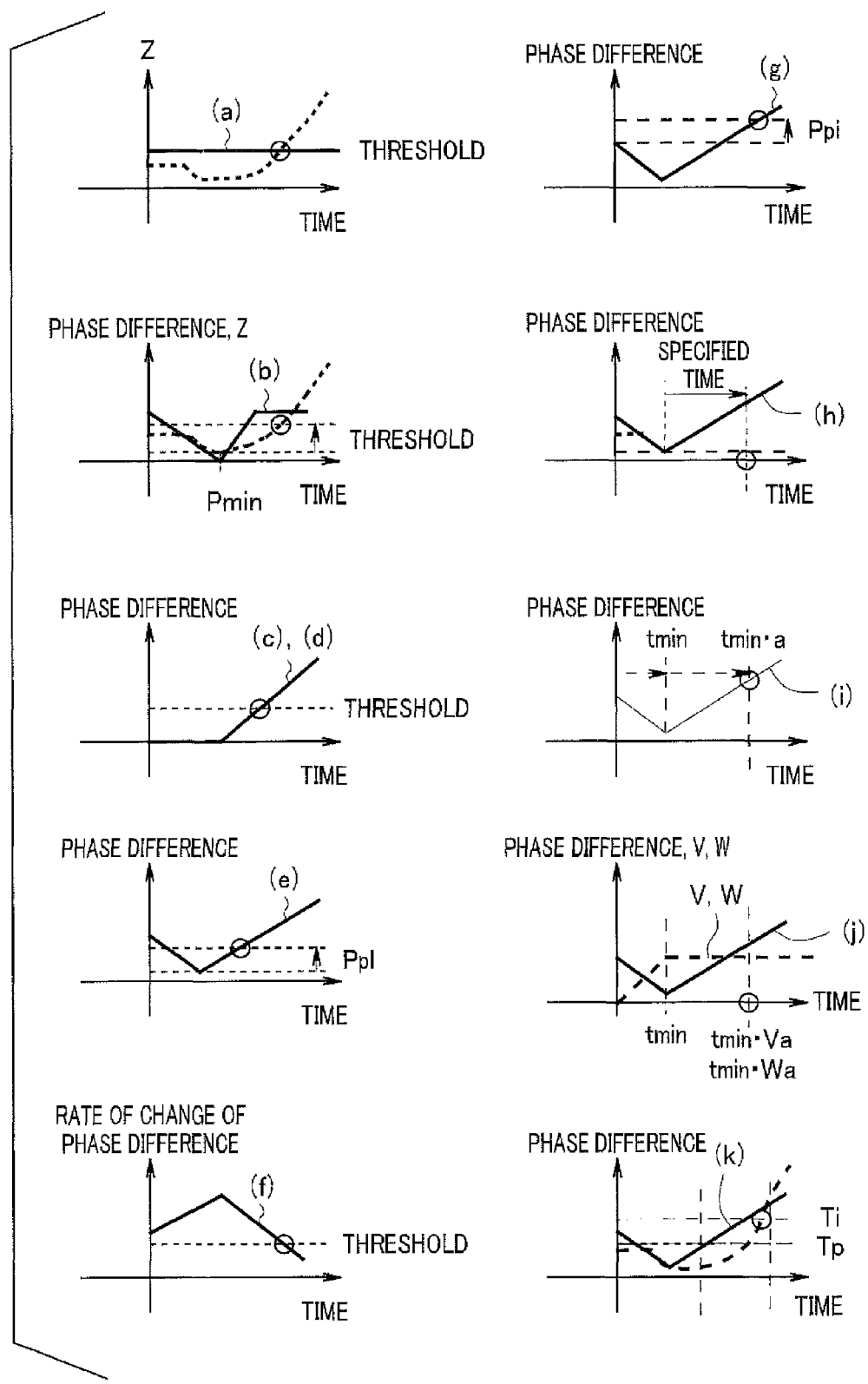
FIG. 8 is an explanatory diagram for explaining output end control.

An operation in the embodiment configured as explained above is explained with referenced to FIG. 4 to FIG. 8. FIG. 4 is a flowchart for explaining the operation in the first embodiment. FIG. 5 is an explanatory diagram for explaining a phase switching method. FIG. 6 is an explanatory diagram for explaining control for the first phase. FIG. 7 is an explanatory diagram for explaining control for the second phase. FIG. 8 is an explanatory diagram for explaining output end control.

In step S1 in FIG. 4, the drying phase, which is the first phase, is started. In a state in which the target tissue 10 is grasped by the treatment instrument 6, the control section 5 controls the high-frequency-power generating section 1 to generate a high-frequency output having predetermined power. The high-frequency output from the output circuit 13 is applied to the target tissue 10 by the treatment instrument 6 via the cable 7 connected to the output terminals 16 and 17. In this way, the drying phase for the target tissue 10 is implemented.

In step S2, the control section 5 gradually increases a voltage of the high-frequency output. That is, the control section 5 includes a first output control section that gradually increases the voltage of the high-frequency output of the high-frequency-power generating section 1. The voltage and an electric current of the high-frequency output are respectively detected by the voltage detecting section 14 and the current detecting section 15. Detection results of the voltage detecting section 14 and the current detecting section 15 are converted into digital signals by the A/D conversion section 3 and thereafter fed back to the control section 5. The control section 5 controls the high-frequency-power generating section 1 on the basis of a fed-back voltage signal and a fed-back current signal such that a specified output is obtained. In this way, in the drying phase, the voltage of the high-frequency output gradually increases as time elapses.

Outputs of the voltage detecting section 14 and the current detecting section 15 are given to the phase-difference detecting section 4. A phase difference between the voltage and the electric current of the high-frequency output is detected by the phase-difference detecting section 4. A detection result of the phase-difference detecting section 4 is supplied to the control section 5 via the A/D conversion section 3. In step S3, the control section 5 determines whether the transition condition based on the phase difference between the voltage and the electric current of the high-frequency output has been satisfied. That is, the control section 5 includes a determining section that determines whether the transition condition based on the phase difference between the voltage and the electric current of the high-frequency output has been satisfied.

Since the high-frequency output is applied to the target tissue 10, moisture of the target tissue 10 gradually decreases. Consequently, capacitance components at both ends of the pair of grasping members of the treatment instrument 6 increase. A phase of the electric current advances on the basis of a phase of the voltage of the high-frequency output. When a predetermined time elapses from the start of the drying phase, the target tissue 10 changes to a sufficiently dried state. For example, phases of the voltage and the electric current of the high-frequency output coincide with each other. Consequently, the control section 5 determines that the phase difference has reached a value that satisfies the transition condition. The control section 5 shifts the processing to step S4. That is, the control section 5 ends the drying phase and shifts to the coaptation phase.

In the coaptation phase, the control section 5 acquires a voltage value of the high-frequency output at an end point in time of the drying phase (step S5) and performs constant voltage control of the output of the high-frequency-power generating section 1 to maintain the voltage value (step S6). That is, the control section 5 includes a second output control section that performs constant voltage control of the output of the high-frequency-power generating section 1.

The target tissue 10 changed to a sufficiently dried state by the drying phase is subjected to coaptation treatment at an optimum voltage corresponding to a final voltage value of the drying phase. In step S7, the control section 5 determines whether the treatment has been completed. The application of the high-frequency output by the constant voltage in step S6 is performed until the coaptation treatment is completed. When the coaptation treatment is completed, the control section 5 ends the processing.

(Phase Switching Method (Transmission-Condition Determining Method))

A switching method for a phase is explained with reference to FIG. 5. In the present embodiment, phase switching methods indicated by (a) to (g) below including the phase switching method explained above may be adopted. Note that characteristics (a) to (d) in FIG. 5 show temporal changes of the absolute value of the phase difference with time plotted on horizontal axes and the absolute value of the phase difference plotted on vertical axes. A characteristic (e) in FIG. 5 shows a current waveform with a broken line and shows a voltage waveform with a solid line with time plotted on a horizontal axis and amplitude plotted on a vertical axis. The characteristics (a) to (f) in FIG. 5 respectively correspond to the switching methods indicated by (a) to (f) below.

(a) Detecting that the phase difference has increased from a state of 0 degree and switching the phase, (b) after the absolute value of the phase difference indicates a minimum value, detecting that the phase difference has increased and switching the phase, (c) detecting that the absolute value of the phase difference has changed from a minus gradient to a plus gradient and switching the phase, (d) detecting that the phase difference has exceeded a specified threshold larger than 0 degree and switching the phase, (e) detecting that phases of the voltage and the electric current have been reversed and switching the phase, and (f) detecting the phase difference and switching the phase when tissue impedance at the time has exceeded a threshold.

In FIG. 5, circle marks indicate points for determining that the phase is switched. For example, in an example of (a) described above, as shown in the characteristic (a) in FIG. 5, a point indicated by the circle mark, that is, a point in time when the absolute value of the phase difference increases from the state of 0 degree is detected and determined as phase switching timing. A transition condition in this case is that the phase difference increases from the state of 0 degree.

Note that the characteristic (e) in FIG. 5 shows a state in which time elapses from a left graph toward a right graph. The graph on the left side indicates that a phase of an electric current (I) is delayed behind a phase of a voltage (V). The graph in the center indicates that the phases of the voltage and the electric current coincide with each other. The graph on the right side indicates that the phase of electric current is advanced ahead of the phase of the voltage. An example of the characteristic (e) in FIG. 5 is an example in which timing in the center graph is set as switching timing. That is, a transition condition is that the phases of the voltage and the electric current are reversed.

In the characteristic (f) in FIG. 5, a solid line indicates a change in the absolute value of the phase difference and a broken line indicates a change in impedance of the target tissue 10. Note that the impedance of the target tissue 10 can be calculated from outputs of the voltage detecting section 14 and the current detecting section 15. In the characteristic (f) in FIG. 5, for example, the condition of (a) described above is determined concerning the phase difference. Further, it is determined whether the impedance has exceeded a threshold. In this way, in an example of (f) described above, timing of the circle mark of the characteristic (f) in FIG. 5 is determined as switching timing of the phase.

(Control Method for the Drying Phase)

A control method for the drying phase is explained with reference to FIG. 6. In the present embodiment, control methods indicated by (a) to (e) below including the control method for the drying phase explained above may be adopted. Note that characteristics (a) to (e) in FIG. 6 respectively correspond to the control methods of (a) to (e) below.

(a) Linearly increasing an output voltage and output power according to time, (b) increasing the output voltage or the output power at specified step width according to time, (c) increasing the output voltage or the output power by a square root according to time, (d) increasing the output voltage or the output power by a square according to time, and (e) intermittently outputting a voltage and power at a fixed duty cycle and increasing the output voltage or the output power in an ON period stepwise.

Graphs in an upper part and a middle part of FIG. 6 show high-frequency outputs in the drying phase with time plotted on horizontal axes and the voltage plotted on vertical axes. A graph in a lower part of FIG. 6 shows a change in the phase difference between the voltage and the electric current of the high-frequency output with the phase difference plotted on a vertical axis. A changing point where the phase difference increases from a minimum value is timing when the first phase is switched to the second phase. Examples of all of the characteristics (a) to (e) in FIG. 6 show control for increasing the voltage or the electric power.

(Control Method for the Coaptation Phase)

A control method for the coaptation phase is explained with reference to FIG. 7. In the present embodiment, control methods indicated by (a) and (b) below including the control method for the coaptation phase explained above may be adopted. Note that characteristics (a) and (b) in FIG. 7 respectively correspond to the control methods of (a) and (b) below.

(a) Setting a voltage value outputted last in the drying phase as a constant voltage value of the coaptation phase.

(b) Acquiring the voltage value outputted last in the drying phase and setting, as the constant voltage value of the coaptation phase, a value obtained by multiplying the voltage value with a coefficient corresponding to a type of the treatment instrument 6. Note that a value of the coefficient corresponds to a grasping area of the grasping member of the treatment instrument 6 and the target tissue 10.

The characteristic (a) and (b) in FIG. 7 show high-frequency outputs in the coaptation phase with time plotted on horizontal axes and the voltage plotted on vertical axes. In both of examples of the characteristics (a) and (b) in FIG. 7, the constant voltage control is performed for the coaptation phase.

Note that the example of the characteristic (b) in FIG. 7 shows an example in which the constant voltage control is performed with a voltage value obtained by reducing a voltage value at the end point in time of the drying phase. However, the constant voltage control may be performed with a voltage value obtained by increasing the voltage value at the end point in time of the drying phase.

(Output End Condition)

An ending method for the coaptation phase is explained with reference to FIG. 8. In the present embodiment, ending methods shown in (a) to (k) below may be adopted as the ending method for the coaptation phase. Note that characteristics (a) to (k) in FIG. 8 respectively correspond to the ending methods of (a) to (k) below.

The characteristics (a) to (k) in FIG. 8 show temporal changes of the phase difference and the impedance with time plotted on horizontal axes and the phase difference, the impedance (Z), and the like plotted on vertical axes. In FIG. 8, circle marks indicate points determined as ends of the coaptation phase.

(a) Detecting that tissue impedance has reached a specified threshold and ending the coaptation phase, (b) setting an impedance threshold from impedance at a time when the phase difference is a minimum value Pmin, detecting that the impedance has reached the impedance threshold, and ending the coaptation phase, (c) detecting that the phase difference has reached a specified threshold and ending the coaptation phase, (d) detecting that the phase difference has reached a threshold set according to a type of a treatment instrument and ending the coaptation phase, (e) detecting that the phase difference has increased by a predefined value PpI from a minimum value and ending the coaptation phase, (f) detecting that a rate of change of the phase difference has decreased to be equal to or smaller than a predefined value and ending the coaptation phase, (g) detecting that the phase difference has reached a threshold Ppi calculated from an initial phase difference and ending the coaptation phase, (h) detecting that a period of the second phase calculated from a period of the first phase has elapsed and ending the coaptation phase, (i) calculating time period tmin·a of the second phase from time period tmin until the phase difference reaches the minimum value, detecting that the time tmin·a has elapsed, and ending the coaptation phase, (j) calculating an output time period of the second phase from a voltage or power value at an end time of the first phase, detecting that the output time has elapsed, and ending the coaptation phase, and (k) detecting that both of the phase difference and the tissue impedance have reached respective specified thresholds Tp and Ti and ending the coaptation phase.

For example, in an example of (a) described above, as shown in the characteristic (a) in FIG. 8, a point indicated by the circle mark, that is, a point in time when the impedance Z has reached the threshold is detected. The point is determined as end timing of the coaptation phase.

In the present embodiment, the switching timings of the respective phases are determined according to the transition conditions based on the phase difference. Irrespective of a type of a treatment target biological tissue, it is surely determined that the biological tissue is in a specified state to enable a shift from the first phase to the second phase. For example, the voltage value at the end point in time of the first phase is set to the voltage value of the constant voltage control of the second phase. The voltage value at the end point in time of the first phase corresponds to the period length of the first phase determined by the transition condition based on the phase difference between the voltage and the electric current of the high-frequency output. The period length of the first phase reflects a state of the biological tissue. By determining the voltage value of the constant voltage control of the second phase according to the period length, it is possible to perform sure treatment for the biological tissue in the second phase. For example, when treatment by the drying phase and the coaptation phase is performed, it is possible to obtain an optimum bonded state of the biological tissue.

First Modification

Figure 9:
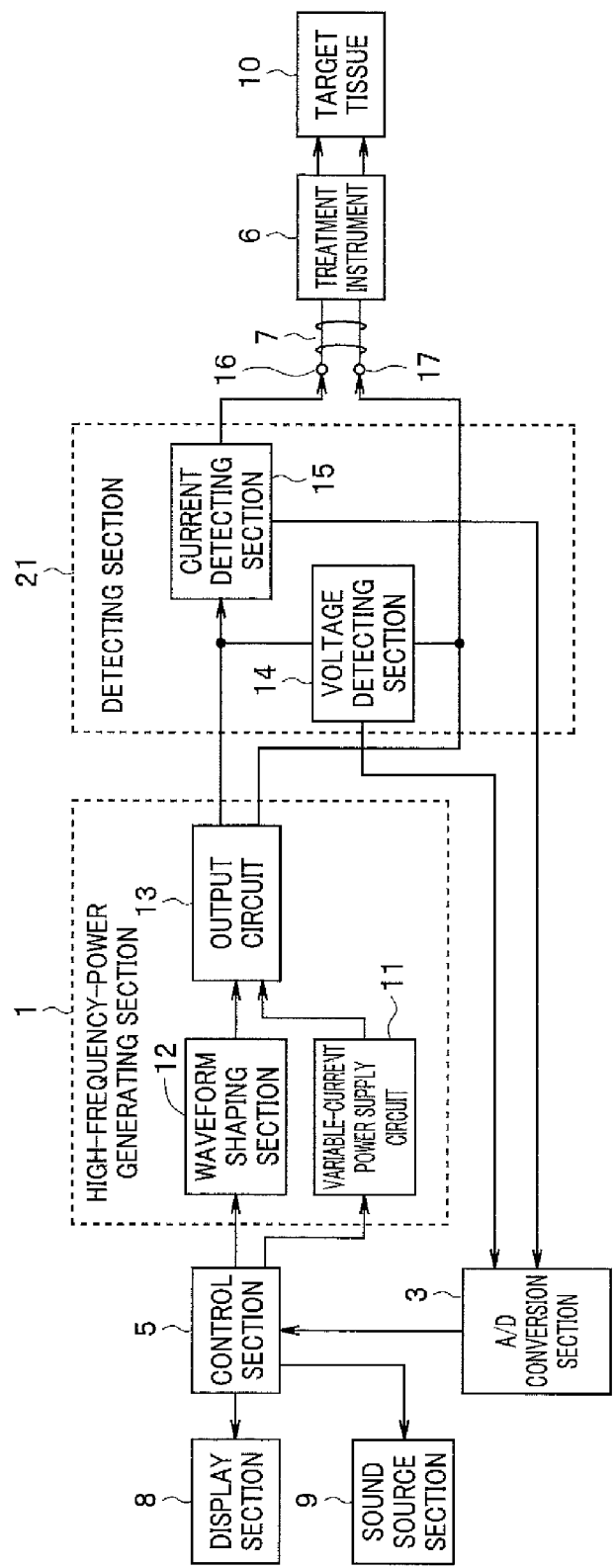
FIG. 9 is a block diagram showing a first modification of the first embodiment.

FIG. 9 is a block diagram showing a first modification of the present embodiment. In FIG. 9, components same as the components shown in FIG. 1 are denoted by the same reference numerals and signs and explanation of the components is omitted. The modification shown in FIG. 9 is only different from the system shown in FIG. 1 in that a detecting section 21 not including the phase-difference detecting section 4 is adopted instead of the detecting section 2.

Outputs of the voltage detecting section 14 and the current detecting section 15 are supplied to the A/D conversion section 3 and converted into a digital signal and thereafter given to the control section 5. The control section 5 calculates the phase difference between the voltage and the electric current of the high-frequency output according to the outputs of the voltage detecting section 14 and the current detecting section 15.

Other components, action, and effects are the same as the components, the action, and the effects in the embodiment shown in FIG. 1.

Second Modification

Figure 10A:
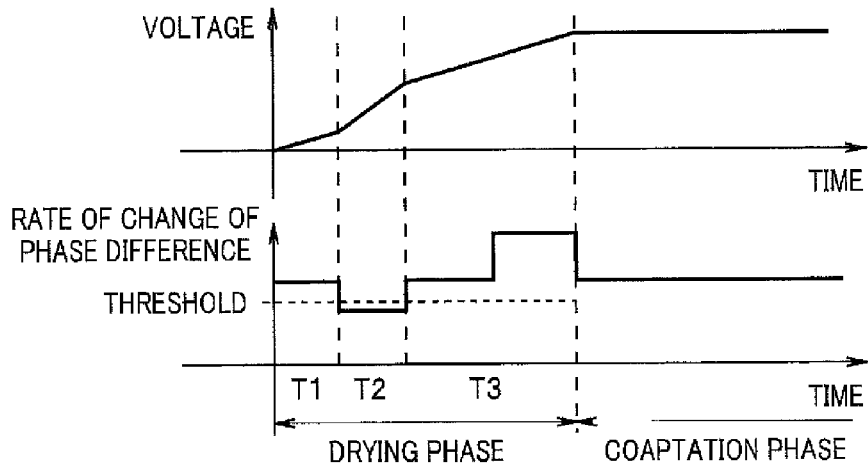
FIG. 10A is an explanatory diagram showing a second modification of the first embodiment.
Figure 10B:
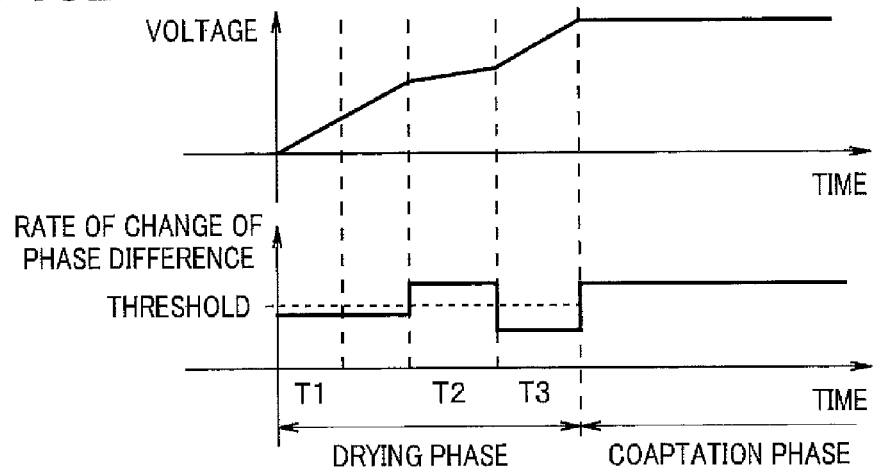
FIG. 10B is an explanatory diagram showing the second modification of the first embodiment.
Figure 10C:
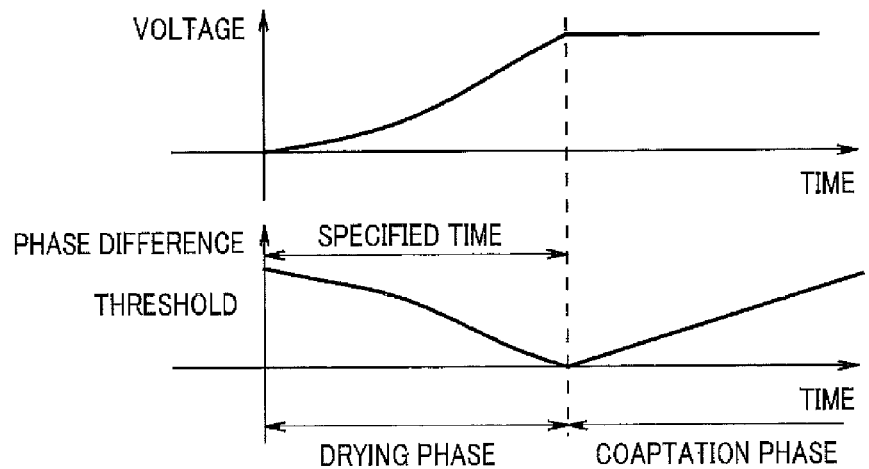
FIG. 10C is an explanatory diagram showing the second modification of the first embodiment.

FIGS. 10A to 10C are explanatory diagrams showing a second modification of the first embodiment. A hardware configuration in the present modification is the same as a hardware configuration shown in FIG. 1 or FIG. 9. This modification indicates still another control example in the drying phase.

In both of FIG. 10A and FIG. 10B, in upper parts, changes in the high-frequency voltage in the drying phase are shown with time plotted on horizontal axes and the voltage plotted on vertical axes. In lower parts, changes in a rate of change of the phase difference in the drying phase are shown with time plotted on horizontal axes and the rate of change of the phase difference plotted on vertical axes. In FIG. 10C, in an upper part, a change in the high-frequency voltage in the drying phase is shown with time plotted on a horizontal axis and the voltage plotted on a vertical axis. In a lower part, a change in the phase difference in the drying phase is shown with time plotted on a horizontal axis and the absolute value of the phase difference plotted on a vertical axis.

In the present modification, the control section 5 is configured to calculate the phase difference between the voltage and the electric current of the high-frequency output and a rate of change of the phase difference and performs voltage control for the high-frequency output in the drying phase according to a change in the phase difference or a change in the rate of change of the phase difference. In an example shown in FIG. 10A, a threshold is set for the rate of change of the phase difference. When the rate of change of the phase difference is larger than the threshold, the control section 5 performs control to increase the voltage of the high-frequency output at a relatively small first gradient, which is initial setting. When the rate of change of the phase difference is smaller than the threshold, the control section 5 performs control to increase the voltage of the high-frequency output at a relatively large second gradient.

In an example shown in FIG. 10A, the rate of change of the phase difference in a period T1 is larger than the threshold. In this case, the control section 5 increases the voltage of the high-frequency output at the first gradient. As shown in a period T2 in FIG. 10A, it is assumed that the rate of change of the phase difference decreases to be smaller than the threshold. In this case, the control section 5 increases the voltage of the high-frequency output at the second gradation larger than the first gradation. Consequently, the voltage of the high-frequency output increases with a relatively large increase amount.

For example, when the target tissue 10 has a relatively high moisture content, it is conceivable that, even if the control section 5 applies the high-frequency output to the target tissue 10 while increasing the voltage at the first gradient set as an initial value of a gradient of a voltage increase in the drying phase, a relatively long time is required for the drying and a drying phase period is relatively long. In this case, the rate of change of the phase difference is considered to decrease. For example, it is conceivable that the rate of change of the phase difference decreases to be smaller than the threshold. Therefore, when the rate of change of the phase difference decreases to be smaller than the threshold, the voltage of the high-frequency output is increased at the second gradient for giving a relatively large voltage increase. Consequently, it is possible to dry the target tissue 10 in a relatively short time.

As a result of the increase in the rate of increase of the voltage of the high-frequency output, when the rate of change of the phase difference increases to exceed the threshold, as shown in a period T3 in FIG. 10A, the control section 5 resets the gradient of the voltage increase of the high-frequency output to the original first gradient. Consequently, it is possible to prevent a high-frequency output having a voltage higher than necessary from being applied to the biological tissue 10.

In an example shown in FIG. 10B as well, a threshold is set for the rate of change of the phase difference. When the rate of change of the phase difference is smaller than the threshold, the control section 5 performs control to increase the voltage of the high-frequency output at a relatively large third gradient, which is initial setting. When the rate of change of the phase difference is larger than the threshold, the control section 5 performs control to increase the voltage of the high-frequency output at a relatively small fourth gradient.

In the example shown in FIG. 10B, the rate of change of the phase difference in the period T1 is smaller than the threshold. In this case, the control section 5 increases the voltage of the high-frequency output at the third gradient. As shown in the period T2 in FIG. 10B, it is assumed that the rate of change of the phase difference increases to be larger than the threshold. In this case, the control section 5 increases the voltage of the high-frequency output at a fourth gradient smaller than the third gradient. Consequently, the voltage of the high-frequency output increases with a relatively small increase amount.

As a result of the decrease in the rate of increase of the voltage of the high-frequency output, when the rate of change of the phase difference decreases to be the threshold or smaller, as shown in the period T3 in FIG. 10B, the control section 5 resets the gradient of the voltage increase of the high-frequency output to the original third gradient. In this way, in the example shown in FIG. 10B as well, it is possible to end the drying phase in a relatively short time while preventing a high-frequency output having a voltage higher than necessary from being applied to the biological tissue 10.

In an example shown in FIG. 10C, the end time of the drying phase is set to a specified time specified in advance. The control section 5 performs control to change the voltage value of the high-frequency output according to a change in a value of the phase difference such that a predetermined transition condition is reached at the specified time period. Consequently, it is possible to end the drying phase in the specified time period.

As a control method for the drying phase, control of (a) and (b) below may be adopted.

(a) Increasing an output voltage or output power according to time. Determining a rate of increase of the output voltage on the basis of a value of an initial phase difference immediately after an output start.

(b) Increasing the output voltage or the output power according to time. Determining a rate of increase of the output voltage on the basis of a value of initial tissue impedance immediately after the output start.

For example, it is conceivable that the control section 5 performs control for making the rate of increase of the output voltage larger as the initial phase difference is larger. For example, it is conceivable that the control section 5 performs control for making the rate of increase of the output voltage larger as the initial tissue impedance is lower.

In the present modification, it is possible to prevent time period required for the drying phase from becoming excessively long.

Second Embodiment

Figure 11:
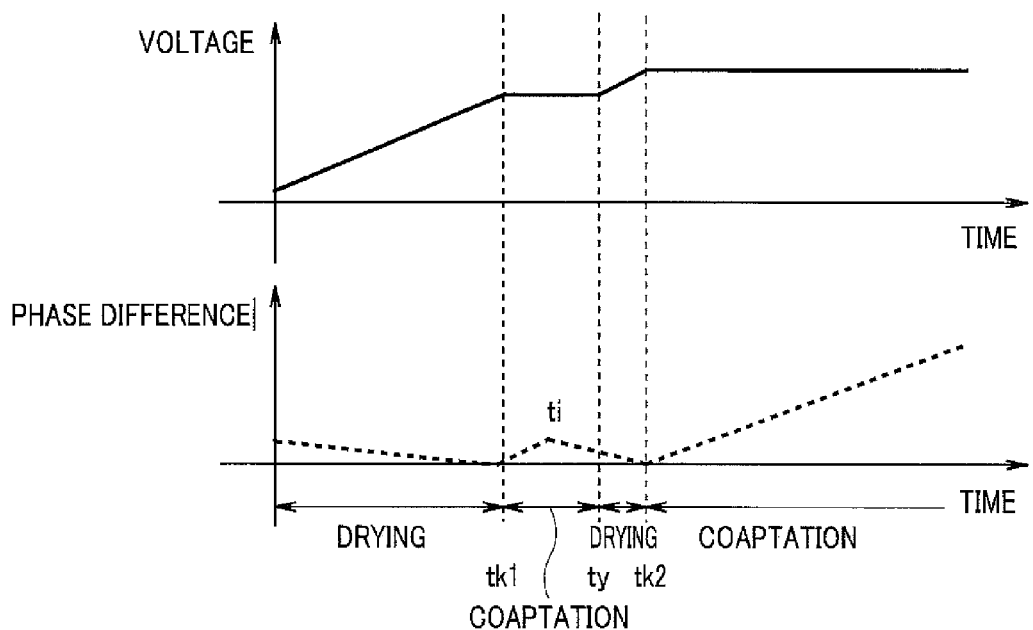
FIG. 11 is an explanatory diagram for explaining control adopted in a second embodiment of the present invention.

FIG. 11 is an explanatory diagram for explaining control adopted in a second embodiment of the present invention. A hardware configuration of the present embodiment is the same as the hardware configuration in the first embodiment.

In the first embodiment, the state of the target tissue is detected according to the phase difference between the voltage and the electric current of the high-frequency output. The first phase is shifted to the second phase when the transition condition based on the phase difference is satisfied. However, since the state of the target tissue is not only affected by the high-frequency output but also affected by, for example, a peripheral environment, it is conceivable that the treatment is desirably returned to the first phase even during the treatment in the second phase. Therefore, in the present embodiment, a transition condition from the second phase to the first phase is determined on the basis of the phase difference to enable effective treatment for the target tissue.

The control section 5 detects whether the absolute value of the phase difference decreases again in the second phase. As explained above, usually, the absolute value of the phase difference decreases from the start of the high-frequency output or stabilizes at a relatively low value. As dehydration and drying of the biological tissue advance, the absolute value of the phase difference increases. In the present embodiment as well, the first phase (the drying phase) is switched to the second phase (the coaptation phase) according to a transition condition same as the transition condition in the first embodiment.

However, the moisture content of the target tissue sometimes increases again while being affected by a grasped state of the target tissue and a peripheral environment such as blood and saline after the shift to the second phase. In this case and the like, the treatment in the first phase is desirably performed again. Therefore, when detecting that the absolute value of the phase difference has decreased again, the control section 5 shifts the phase from the second phase to the first phase. Note that subsequent switching from the first phase to the second phase is performed in the same manner as in the first embodiment.

An upper part of FIG. 11 shows a change in the voltage of the high-frequency output with time plotted on a horizontal axis and the voltage plotted on a vertical axis. A lower part of FIG. 11 shows a change in the phase difference between the voltage and an electric current of the high-frequency output with time plotted on a horizontal axis and the absolute value of the phase difference plotted on a vertical axis. In the first drying phase, the control section 5 increases the voltage of the high-frequency output. The drying of the target tissue 10 advances and the absolute value of the phase difference gradually decreases. When a value of the absolute value of the phase difference reaches a value satisfying the transition condition at timing tk1, the control section 5 shifts the phase from the drying phase to the coaptation phase and performs constant voltage control by a voltage value at the end point in time of the drying phase.

Subsequently, it is assumed that, at timing ti, the moisture content of the target tissue 10 increases because of some reason. Then, the influence of the inductance component of the cable 7 increases and a phase of the electric current of the high-frequency output is delayed compared with a phase of the voltage. However, since the high-frequency output is applied to the target tissue 10 in the coaptation phase, the phase of the electric current advances little by little.

In the present embodiment, in the coaptation phase, when detecting a state in which, from a state in which the phase of the electric current is delayed compared with the phase of the voltage, the phase of the electric current advances and approaches the phase of the voltage, that is, a state in which the absolute value of the phase decreases, the control section 5 determines that the transition condition for shifting to the drying phase has been satisfied and performs control corresponding to the drying phase. For example, in an example shown in the upper part of FIG. 11, the control section 5 determines that the transition condition for shifting from the coaptation phase to the drying phase has been satisfied at timing ty and shifts to the drying phase. The control section 5 sets a voltage at the switching timing as a start voltage in the drying phase and gradually increases a voltage value.

Consequently, the absolute value of the phase difference gradually decreases. When determining that the transition condition from the first phase to the second phase has been satisfied at timing tk2, the control section 5 shifts to the coaptation phase again. In the second time of the coaptation phase, the control section 5 performs the constant voltage control by a voltage value at an end point in time of the second time of the drying phase.

Note that, in the example shown in FIG. 11, an example is shown in which the control section 5 detects that the absolute value of the phase difference has decreased by a predetermined value or more and determines that the transition condition from the second phase to the first phase has been satisfied. However, the control section 5 may immediately shift the second phase to the first phase at a point in time when the absolute value of the phase difference starts to decrease.

In this way, in the present embodiment, the control section 5 detects according to the change in the phase difference between the voltage and the electric current of the high-frequency output that the moisture content of the target tissue increases after the shift to the second phase. The control section 5 performs control to shift to the first phase again. Consequently, it is possible to perform effective treatment by the first phase and the second phase.

Third Embodiment

Figure 12:
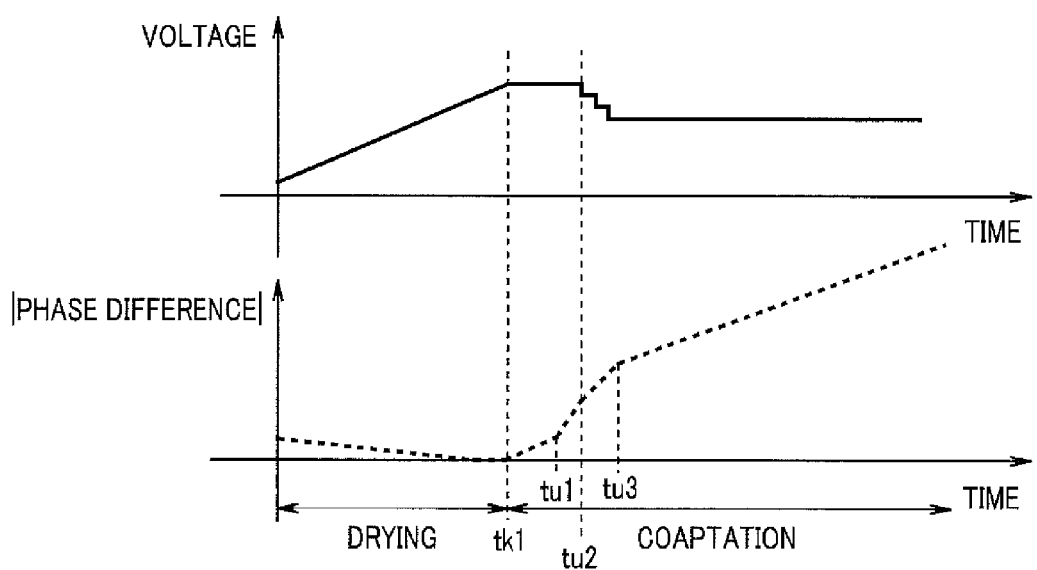
FIG. 12 is an explanatory diagram for explaining control adopted in a third embodiment of the present invention.

FIG. 12 is an explanatory diagram for explaining control adopted in a third embodiment of the present invention. A hardware configuration in the present embodiment is the same as the hardware configuration in the first embodiment.

In the first embodiment, the example is explained in which the constant voltage control is performed in the second phase (the coaptation phase). When the target tissue is a thin tissue or when a tissue having a relatively low moisture content is treated, it is conceivable that drying suddenly advances when the constant voltage control is performed. Therefore, in the present embodiment, the voltage value of the high-frequency output is reduced when the rate of increase of the absolute value of the phase difference increases to be larger than a predetermined threshold in the second phase.

The control section 5 detects whether the rate of increase of the absolute value of the phase difference increases to be larger than the predetermined threshold in the second phase. When detecting that the rate of increase of the absolute value of the phase difference has increased to be larger than the predetermined threshold, the control section 5 performs control to end the constant voltage control of the high-frequency output and gradually decrease the voltage value. As a result of the control, when the rate of increase of the absolute value of the phase difference decreases to be smaller than the predetermined threshold, the control section 5 returns to the constant voltage control in which the voltage value at a point in time of the detection is maintained. Note that the switching from the first phase to the second phase is performed in the same manner as in the first embodiment.

An upper part of FIG. 12 shows a change in the voltage of the high-frequency output with time plotted on a horizontal axis and the voltage plotted on a vertical axis. A lower part of FIG. 12 shows a change in the phase difference between the voltage and the electric current of the high-frequency output with time plotted on a horizontal axis and the absolute value of the phase difference plotted on a vertical axis. In the drying phase, the control section 5 increases the voltage of the high-frequency output. The drying of the target tissue 10 advances and the absolute value of the phase difference gradually decreases. When a value of the absolute value of the phase difference reaches a value satisfying the transition condition at timing tk1, the control section 5 shifts the phase from the drying phase to the coaptation phase and performs constant voltage control by a voltage value at the end point in time of the drying phase.

Subsequently, it is assumed that, at timing tut, the moisture content of the target tissue 10 suddenly decreases because of some reason. Then, the absolute value of the phase difference between the voltage and the electric current of the high-frequency output suddenly increases. As a result, the control section 5 detects that the rate of increase of the absolute value of the phase difference has exceeded a predetermined threshold at timing tu2. In this case, the control section 5 performs the control for reducing the voltage value of the high-frequency output in the coaptation phase as well. The upper part of FIG. 12 indicates that the control for reducing the voltage value stepwise has been performed at timing tu2 and subsequent timing.

As a result of reducing the voltage value of the high-frequency output, the rate of increase of the absolute value of the phase difference decreases. When detecting that the rate of increase of the absolute value of the phase difference has decreased to be smaller than the predetermined threshold at timing tu3, the control section 5 returns to the constant voltage control in which the voltage value at the point in time is maintained.

In this way, in the present embodiment, when it is detected according to the change in the phase difference between the voltage and the electric current of the high-frequency output that the moisture content of the target tissue has suddenly decreased after the shift to the second phase, even in the second phase, the control for reducing the voltage value of the high-frequency output is performed. Consequently, it is possible to perform treatment for drying the target tissue at appropriate speed.

First Modification

Figure 13:
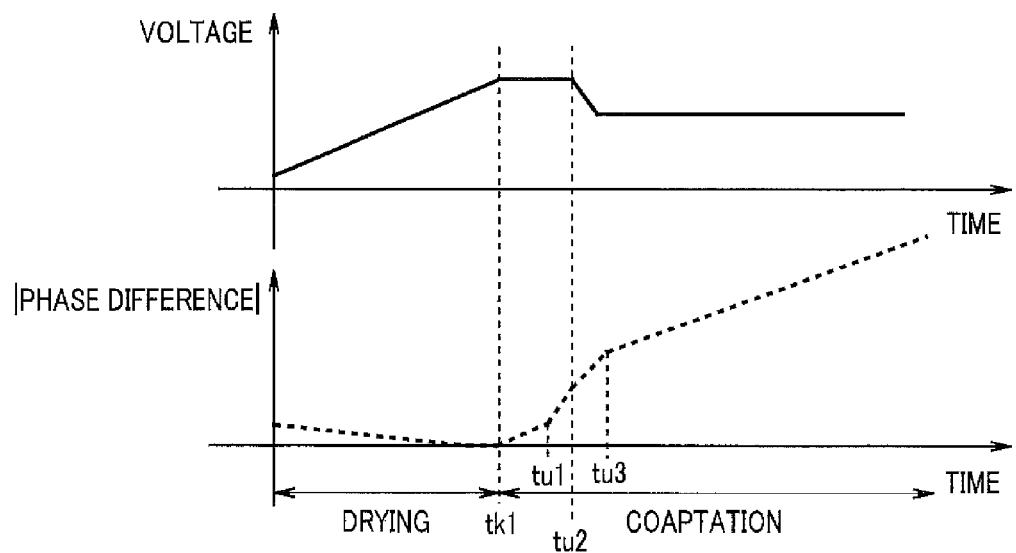
FIG. 13 is an explanatory diagram showing a first modification of the third embodiment.

FIG. 13 is an explanatory diagram showing a first modification of the third embodiment. In FIG. 13, graphs are written the same as the graphs of FIG. 12. An example shown in FIG. 13 is only different from the example shown in FIG. 12 in that, in the second phase, when it is detected that the rate of increase of the absolute value of the phase difference has increased to be larger than the predetermined threshold, control is performed to end the constant voltage control of the high-frequency output and reduce the voltage value in a linear function manner.

Second Modification

Figure 14:
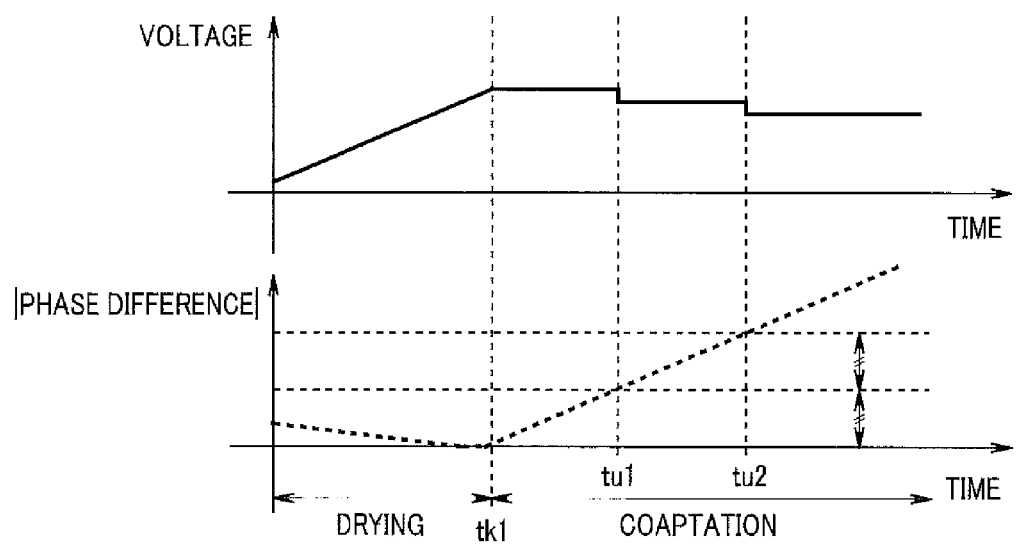
FIG. 14 is an explanatory diagram showing a second modification of the third embodiment.

FIG. 14 is an explanatory diagram showing a second modification of the third embodiment. In the example shown in FIG. 12, in the second phase, when it is detected that the rate of increase of the absolute value of the phase difference has increased to be larger than the predetermined threshold, the control is performed to end the constant voltage control for the high-frequency output and reduce the voltage value, for example, stepwise until the rate of increase of the absolute value of the phase difference decreases to be smaller than the predetermined threshold.

On the other hand, in the modification, a state of drying in the second phase is detected according to the absolute value of the phase difference. Every time a change amount of the absolute value of the phase difference reaches a predetermined amount, the voltage value of the high-frequency output is reduced stepwise.

The control section 5 detects whether the change amount of the absolute value of the phase difference has reached a specified value in the second phase. When detecting that the change amount of the absolute value of the phase difference has reached the specified value, the control section 5 performs control to reduce the high-frequency output by a predetermined voltage value. Thereafter, the control section 5 repeats the same control in the second phase. Note that the switching from the first phase to the second phase is performed in the same manner as in the first embodiment.

An upper part of FIG. 14 shows a change in the voltage of the high-frequency output with time plotted on a horizontal axis and the voltage plotted on a vertical axis. A lower part of FIG. 14 shows a change in the phase difference between the voltage and the electric current of the high-frequency output with time plotted on a horizontal axis and the absolute value of the phase difference plotted on a vertical axis. The control section 5 increases the voltage of the high-frequency output in the drying phase. The drying of the target tissue 10 advances and the absolute value of the phase difference gradually decreases. When the change in the phase difference satisfies the transition condition at timing tk1, the control section 5 shifts the phase from the drying phase to the coaptation phase and performs constant voltage control by a voltage value at the end point in time of the drying phase.

According to the constant voltage control, the drying of the target tissue 10 advances and the absolute value of the phase difference gradually increases. For example, when the target tissue 10 is a relatively thin tissue, it is conceivable that the drying advances too quickly. Therefore, in the present embodiment, the control section 5 determines whether the change amount of the absolute value of the phase difference has reached a specified value. An example shown in the lower part of FIG. 14 indicates that the change amount of the absolute value of the phase difference after the shift to the coaptation phase has exceeded the specified value at timing tu1. When detecting that the change amount of the absolute value of the phase difference has reached the specified value, the control section 5 reduces the high-frequency output by a predetermined voltage value and thereafter performs the constant voltage control.

An example shown in the lower part of FIG. 14 indicates that the change amount of the absolute value of the phase difference at timing tu1 and subsequent timing has exceeded the specified value at timing tut. When detecting that the change amount of the absolute value of the phase difference has reached the specified value, the control section 5 further reduces the high-frequency output by the predetermined voltage value and thereafter performs the constant voltage control.

In this way, in the present modification, to prevent the moisture content of the target tissue from suddenly decreasing after the shift to the second phase, every time the change amount of the phase difference between the voltage and the electric current of the high-frequency output reaches the specified value, even in the second phase, the control for reducing the voltage value of the high-frequency output stepwise is performed. Consequently, it is possible to perform treatment for drying the target tissue at appropriate speed.

Fourth Embodiment

Figure 15:
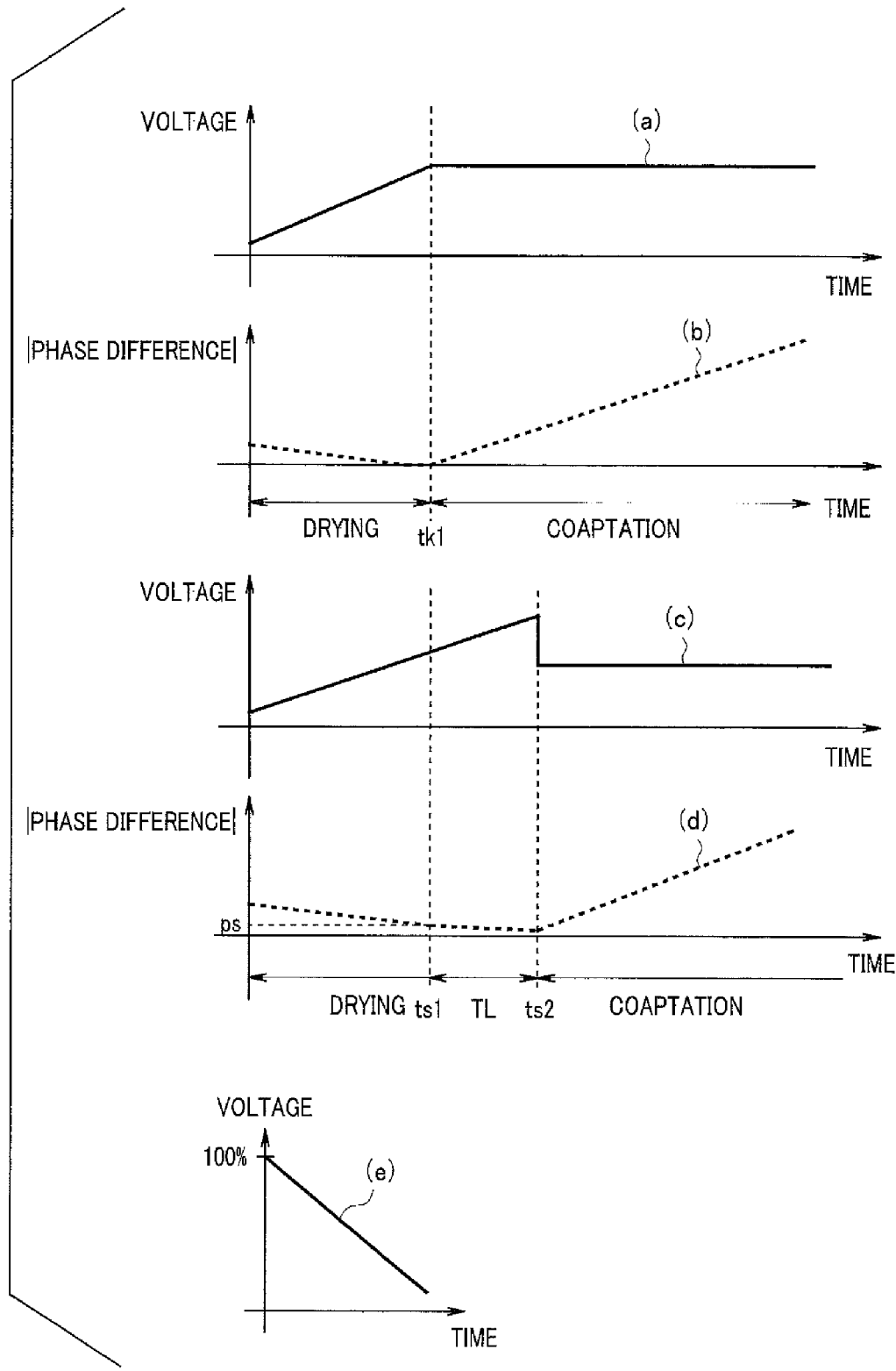
FIG. 15 is an explanatory diagram for explaining control adopted in a fourth embodiment of the present invention.

FIG. 15 is an explanatory diagram for explaining control adopted in a fourth embodiment of the present invention. A hardware configuration in the present embodiment is the same as the hardware configuration in the first embodiment.

In the first embodiment, the example is explained in which, for example, the voltage value of the high-frequency output is gradually increased in the first phase (the coaptation phase) and the constant voltage control in which the voltage value at the end point in time of the first phase is maintained is performed in the second phase. However, when the target tissue is relatively thick or when a tissue having a relatively high moisture content is treated, it is conceivable that the first phase period is relatively long and the voltage value in the second phase increases to an excessive level. Therefore, in the present embodiment, after the phase difference sufficiently decreases, when time period until the transition condition is satisfied is relatively long, it is determined that the voltage value at the end point in time of the first phase has reached an excessively high level. The voltage value in the second phase is reduced to be smaller than the voltage value at the end point in time of the first phase. The constant voltage control is performed for the second phase.

The control section 5 calculates time ts1 when the absolute value of the phase difference has reached a value equal to or smaller than a predetermined threshold ps in the first phase. The control section 5 calculates time ts2 at a point in time when, in the first phase, the absolute value of the phase difference has satisfied the transition condition for the shift to the second phase. The control section 5 calculates a time period TL (=ts2−ts1) required until the absolute value of the phase difference has satisfied the transition condition after reaching the predetermined threshold ps. Note that the threshold ps is set to a value near the absolute value of the phase difference that satisfies the transition condition. The control section 5 calculates a voltage decrease value reduced in the second phase according to the time period TL. In the second phase, the control section 5 performs the constant voltage control with a voltage reduced from a voltage at the end point in time of the first phase by the voltage decrease value. Note that the switching from the first phase to the second phase is performed in the same manner as in the first embodiment.

Note that, when the time period TL is shorter than a predetermined threshold time, the control section 5 may perform the constant voltage control for the second phase with the voltage value at the end point in time of the first phase. Characteristics (a) and (b) in FIG. 15 show control in this case. The characteristic (a) in FIG. 15 shows a change in the voltage of the high-frequency output with time plotted on a horizontal axis and the voltage plotted on a vertical axis. The characteristic (b) in FIG. 15 shows a change in the phase difference between the voltage and the electric current of the high-frequency output with time plotted on a horizontal axis and the absolute value of the phase difference plotted on a vertical axis. Control of the characteristics (a) and (b) in FIG. 15 is the same as the control in the first embodiment. In the second phase, the constant voltage control in which the voltage value at the end point in time of the first phase is used is performed.

Characteristics (c) and (d) in FIG. 15 show control performed when the time period TL exceeds a predetermined threshold or control performed when the voltage value in the second phase is changed according to the time period TL. The characteristic (c) in FIG. 15 shows a change in the voltage of the high-frequency output with time plotted on a horizontal axis and the voltage plotted on a vertical axis. The characteristic (c) in FIG. 15 shows a change in the phase difference between the voltage and the electric current of the high-frequency output with time plotted on a horizontal axis and the absolute value of the phase difference plotted on a vertical axis.

In the drying phase, the control section 5 increases the voltage of the high-frequency output. The drying of the target tissue 10 advances and the absolute value of the phase difference gradually decreases. The absolute value of the phase difference reaches the predetermined threshold ps at timing ts1. For example, when the target tissue 10 is relatively thick, a relatively long time sometimes elapses until the absolute value of the phase difference satisfies the transition condition after reaching the threshold ps. An example of the characteristic (b) in FIG. 15 indicates that, after the time period TL after the absolute value of the phase difference reaches the predetermined threshold ps, the absolute value of the phase difference reaches the absolute value of the phase difference that satisfies the transition condition. In this case, since the drying phase is relatively long, the voltage value at the end point in time of the drying phase is a relatively high value. In the present embodiment, as shown in the characteristic (c) in FIG. 15, the control section 5 performs the constant voltage control with a voltage reduced by a voltage corresponding to the time period TL from the voltage at the end point in time of the drying phase.

A characteristic (e) in FIG. 15 shows an example of setting of the voltage value of the high-frequency output in the second phase (the coaptation phase). The characteristic (e) in FIG. 15 shows a relation between the time period TL required until the absolute value of the phase difference satisfies the transition condition after reaching the threshold ps and the voltage set in the second phase with time plotted on a horizontal axis and the voltage plotted on a vertical axis. In an example of the characteristic (e) in FIG. 15, as the time period TL increases, the voltage value of the constant voltage control in the second phase is reduced.

In this way, in the present embodiment, control for reducing the voltage value of the high-frequency output of the second phase according to the time period until the absolute value of the phase difference satisfies the transition condition after reaching the value near the value that satisfies the transition condition is performed. Consequently, it is possible to perform treatment for drying the target tissue at appropriate speed.

Incidentally, it is necessary to manage surface temperature of a treatment instrument that grasps a biological tissue. Temperature on a treatment instrument outer surface depends on an energy amount supplied to the treatment instrument. That is, it is possible to calculate the temperature on the treatment instrument outer surface according to a product of electric power applied to the treatment instrument and time. Actually, a temperature rise on the outer surface of the treatment instrument has a time lag with respect to energy supplied to the treatment instrument. Therefore, the treatment instrument outer surface temperature is calculated taking into account the time lag.

Figure 16:
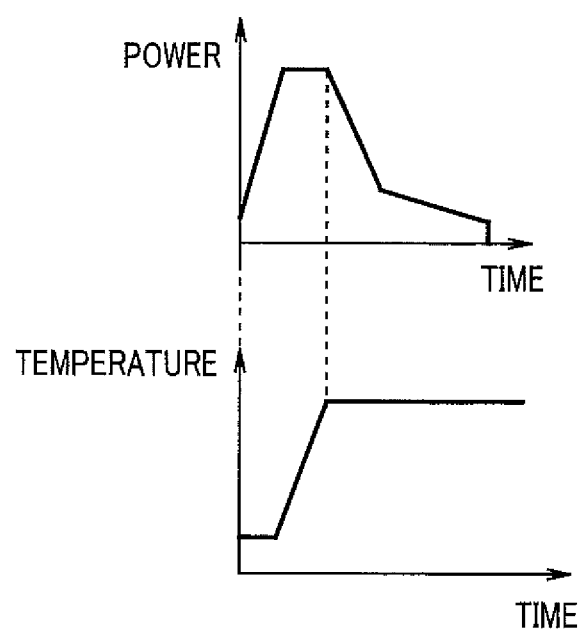
FIG. 16 is an explanatory diagram showing an example of power control for fixing a treatment instrument outer surface temperature.

FIG. 16 is an explanatory diagram showing an example of power control for fixing the treatment instrument outer surface temperature. An upper part of FIG. 16 shows the electric power applied to the treatment instrument with time plotted on a horizontal axis and the electric power plotted on a vertical axis. A lower part of FIG. 16 shows a change in the temperature on the treatment instrument outer surface with time plotted on a horizontal axis and the temperature plotted on a vertical axis. Note that the upper part and the lower part of FIG. 16 are shown using a common time axis.

As shown in FIG. 16, a rise in the temperature on the treatment instrument outer surface starts after a slight delay time with respect to power supply to the treatment instrument. Even if the electric power supplied to the treatment instrument is fixed, the temperature rise on the treatment instrument outer surface continues. By reducing the electric power applied to the treatment instrument, it is possible to fix the temperature on the treatment instrument outer surface. For example, when the electric power is changed as shown in the upper part of FIG. 16, it is possible to fix the temperature on the treatment instrument outer surface. Such control is enabled by calculation of the energy amount supplied to the treatment instrument.

It is possible to calculate the surface temperature of the treatment instrument outer surface by performing such calculation and perform, on the basis of a result of the calculation, display of a present temperature, forced power restriction, and the like.

It is also possible to calculate the treatment instrument outer surface temperature using a correspondence table or a relational expression of a cumulative supplied energy amount and the treatment instrument outer surface temperature. In this case, it is possible to perform temperature control irrespective of a treatment instrument by storing the correspondence table or the relational expression for each of treatment instruments.

For example, when the calculated treatment instrument outer surface temperature exceeds a first threshold, warning may be emitted. When the calculated treatment instrument outer surface temperature exceeds a second threshold, the power supply to the treatment instrument may be limited. For example, when the calculated treatment instrument outer surface temperature exceeds the first threshold, a power supply amount to the treatment instrument may be limited to be reduced. When the calculated treatment instrument outer surface temperature exceeds the second threshold, the power supply amount to the treatment instrument may be limited to be further reduced.

Consequently, it is possible to use the treatment instrument at proper outer surface temperature.

Note that, in the respective embodiments, the example is explained in which the high-frequency output is continuously applied to the biological tissue in the second phase. However, control may be performed to intermittently apply the high-frequency output to the biological tissue.

According to the respective embodiments, the switching from the first phase to the second phase is determined according to the phase difference between the electric current and the voltage of the high-frequency output applied to the treatment target. The level of the high-frequency output in the second phase is set to the level corresponding to the period length of the first phase period. Consequently, the embodiments have an effect that it is possible to enable sure and stable treatment irrespective of a treatment target tissue.

The present invention is not limited to the respective embodiments per se. The constituent elements can be modified and implemented without departing from the spirit of the present invention in an implementation stage. Various inventions can be formed by appropriate combinations of the plurality of constituent elements disclosed in the respective embodiments. For example, several constituent elements of all the constituent elements described in the embodiments may be deleted. Further, the constituent elements described in the different embodiments may be combined as appropriate.

What is claimed is:

1. An electrosurgical treatment system for use with a biological tissue and for use with a treatment instrument, the electrosurgical treatment system comprising:
   a high-frequency-power generator that generates a high-frequency output for treating the biological tissue;
   an output section that supplies the high-frequency output to the treatment instrument that applies the high-frequency output to the biological tissue;
   a detector that detects a voltage and an electric current of the high-frequency output in the output section;
   a phase-difference detector that calculates a phase difference between the voltage and the electric current detected by the detector; and
   a processor programmed to:
      in response to a change in the phase difference calculated by the phase-difference detector, control the high-frequency-power generator to switch from: (i) a first phase for drying the biological tissue by applying the high-frequency output in the output section to the biological tissue while continuously or discontinuously increasing the voltage with respect to a start time, to (ii) a second phase for coapting the biological tissue by performing voltage control such that the high-frequency output to be applied to the biological tissue is maintained at a constant voltage of a set voltage value that is determined based on a voltage value at an end point in time of the first phase, and (iii) return the high-frequency output to the first phase for drying the biological tissue,
   wherein the processor switches the first phase to the second phase on the basis of an absolute value of the phase difference starting to increase, and the processor switches from the second phase to the first phase on the basis of the absolute value of the phase difference decreasing.

2. The electrosurgical treatment system according to claim 1, wherein the processor switches the first phase to the second phase on the basis of an absolute value of the phase difference increasing and reaching a predetermined threshold.

3. The electrosurgical treatment system according to claim 1, wherein the processor switches the first phase to the second phase on the basis of an absolute value of the phase difference indicating a minimum value and thereafter increasing.

4. The electrosurgical treatment system according to claim 1, wherein, in the first phase, the processor intermittently or continuously increases the voltage of the high-frequency output.

5. The electrosurgical treatment system according to claim 1, wherein, in the first phase, the processor changes a rate of increase of the voltage of the high-frequency output according to a rate of change of the phase difference.

6. The electrosurgical treatment system according to claim 1, wherein, in the second phase, the processor performs the constant voltage control in which a voltage value of the high-frequency output at an end point in time of the first phase is maintained.

7. The electrosurgical treatment system according to claim 1, wherein, in the second phase, the processor performs the constant voltage control in which a voltage value obtained by reducing or increasing a voltage value of the high-frequency output at an end point in time of the first phase is maintained.

8. The electrosurgical treatment system according to claim 1, wherein the processor is capable of switching the first phase and the second phase a plurality of times on the basis of the change in a phase difference.

9. The electrosurgical treatment system according to claim 1, wherein the processor changes a set value of a voltage of the constant voltage control on the basis of a change in the phase difference in the second phase.

10. The electrosurgical treatment system according to claim 1, wherein, when a rate of change of the phase difference in the second phase is larger than a predetermined threshold, the processor reduces a set value of a voltage of the constant voltage control stepwise or continuously.

11. The electrosurgical treatment system according to claim 1, wherein the processor reduces a set value of a voltage of the constant voltage control every time the phase difference changes by a specified value in the second phase.

12. An electrosurgical treatment system for use with a biological tissue and for use with a treatment instrument, the electrosurgical treatment system comprising:
   a high-frequency-power generator that generates a high-frequency output for treating the biological tissue;
   an output section that supplies the high-frequency output to the treatment instrument that applies the high-frequency output to the biological tissue;
   a detector that detects a voltage and an electric current of the high-frequency output in the output section; and
   a processor programmed to:
      calculate a phase difference between the voltage and the electric current detected by the detector; and
      in response to a change in the calculated phase difference, control the high-frequency power generator to switch from: (i) a first phase for drying the biological tissue by applying the high-frequency output in the output section to the biological tissue while continuously or discontinuously increasing the voltage with respect to a voltage at a start time, to (ii) a second phase for coapting the biological tissue by performing voltage control such that the high-frequency output to be applied to the biological tissue is maintained at a constant voltage of a set voltage value that is determined according to a voltage value at an end point in time of the first phase, and (iii) return the high-frequency output to the first phase for drying the biological tissue,
   wherein the processor switches the first phase to the second phase on the basis of an absolute value of the phase difference starting to increase, and the processor switches from the second phase to the first phase on the basis of the absolute value of the phase difference decreasing.

13. An electrosurgical treatment system for use with a biological tissue and for use with a treatment instrument, the electrosurgical treatment system comprising:
   a high-frequency-power generator that generates a high-frequency output for treating the biological tissue;
   an output section that supplies the high-frequency output to the treatment instrument that applies the high-frequency output to the biological tissue;
   a detector that detects a voltage and an electric current of the high-frequency output in the output section;
   a phase-difference detector that calculates a phase difference between the voltage and the electric current detected by the detector; and
   a processor programmed to:
      in response to a change in the phase difference calculated by the phase-difference detector, control the high-frequency-power generator to switch from: (i) a first phase for drying the biological tissue by applying the high-frequency output in the output section to the biological tissue while continuously or discontinuously increasing the voltage with respect to a start time, to (ii) a second phase for coapting the biological tissue by performing voltage control such that the high-frequency output to be applied to the biological tissue is maintained at a constant voltage of a set voltage value that is determined based on a voltage value at an end point in time of the first phase, wherein in the second phase, the processor performs the voltage control at a voltage value reduced by a voltage value corresponding to a period length of the first phase from a voltage at an end point in time of the first phase.

* * * * *